United States Patent [19]
Buschle et al.

[11] Patent Number: 5,965,404
[45] Date of Patent: Oct. 12, 1999

[54] METHOD FOR INTRODUCING NUCLEIC ACIDS INTO HIGHER EUKARYOTIC CELLS

[75] Inventors: Michael Buschle, Brunn am Gebirge; Ernst Wagner, Langenzersdorf; Wolfgang Zauner, Vienna, all of Austria

[73] Assignee: Boehringer Ingelheim International FmbH, Ingelheim am Rhein, Germany

[21] Appl. No.: 08/750,181
[22] PCT Filed: May 24, 1995
[86] PCT No.: PCT/EP95/01969
  § 371 Date: Mar. 6, 1997
  § 102(e) Date: Mar. 6, 1997
[87] PCT Pub. No.: WO95/33061
  PCT Pub. Date: Dec. 7, 1995

[30] Foreign Application Priority Data

May 31, 1994 [DE] Germany .............................. 44 18 965

[51] Int. Cl.$^6$ .............................. C12N 15/63; C12N 5/16
[52] U.S. Cl. .................... 435/69.52; 435/70.1; 435/70.3; 435/325; 435/357; 435/320.1
[58] Field of Search .............................. 435/69.52, 70.1, 435/70.3, 325, 357, 320.1

[56] References Cited

U.S. PATENT DOCUMENTS

| | | | |
|---|---|---|---|
| 4,608,339 | 8/1986 | Yoakum et al. | 435/172.2 |
| 4,652,522 | 3/1987 | Kennett et al. | 435/68 |
| 5,254,342 | 10/1993 | Shen et al. | 424/401 |
| 5,354,844 | 10/1994 | Beug et al. | 530/345 |
| 5,521,291 | 5/1996 | Curiel et al. | 530/391.7 |
| 5,547,932 | 8/1996 | Curiel et al. | 435/65 |

FOREIGN PATENT DOCUMENTS

| | | |
|---|---|---|
| 0 257 993 | 3/1988 | European Pat. Off. . |
| 63-102682 | 5/1988 | Japan . |
| WO 91/00915 | 1/1991 | WIPO . |
| WO 92/05262 | 4/1992 | WIPO . |
| WO 93/07283 | 4/1993 | WIPO . |
| WO 93/19768 | 10/1993 | WIPO . |

OTHER PUBLICATIONS

Reaves, et al. FEBS Lett. vol. 345: pp. 61–66, 1994.
International Preliminary Examination Report for Application No. PCT/EP95/01969, mailed Nov. 1996.
Dialog file 351, Derwent World Patents Index, English language abstract for JP 63–102682, WPI Accession No. 88–164720 (1988).
Arnold, K. et al., "The dielectric properties of aqueous solutions of poly(ethylene glycol) and theirinfluence on membrane structure," *Biochim. Biophys. Acta* 815:515–518 (1985).
Akopian, T.A. et al., "Sequence of an Avian Adenovirus (CELO) DNA Fragment (11–2–19.2%)," EMBL Database Accession No. Z22864 (Jun. 1993).
Chiou, S.–K. et al., "Functional Complementation of the Adenovirus E1B 19–Kilodalton Protein with Bcl–2 in the Inhibition of Apoptosis in Infected Cells," *J. Virol.* 68(10):6553–6566 (Oct. 1994).
Cotten, M. et al., "Transferrin–polycation–mediated introduction of DAN into human leukemic cells: Stimulation by agents that affect the survival of transfected DNA or modulate transferrin receptor levels," *Proc. Natl. Acad. Sci. USA* 87:4033–4037 (1990).
Curiel, D.T. et al., "High–Efficiency Gene Transfer Mediated by Adenovirus Coupled to DNA–Polylysine Complexes," *Human Gene Ther.* 3:147–154 (1992).
Debbas, M. and E. White, "Wild–type p53 mediates apoptosis by E1A, which is inhibited by E1B," *Genes & Dev.* 7:546–554 (Apr. 1993).
Miyashita, T. and J.C. Reed, "*bcl*–2 Gene Transfer Increases Relative Resistance of S49.1 and WEHI7.2 Lymphoid Cells to Cell Death and DNA Fragmentation Induced by Glucocorticoids and Multiple Chemotherapeutic Drugs," *Can. Res.* 52:5407–5411 (1992).
Rao, L. et al., "The adenovirus E1A proteins induce apoptosis, which is inhibited by the E1B 19–kDa and Bcl–2 proteins," *Proc. Natl. Acad. Sci. USA* 89:7742–7746 (1992).
Staedel, C. et al., "High–Efficiency Transfection of Primary Human Keratinocytes with Positively Charged Lipopolyamine:DNA Complexes," *J. Invest, Dermatol.* 102:768–772 (May 1994).
Zatloukal, K. et al., "Transferrinfection: A Highly Efficient Way to Express Gene Constructs in Eukaryotic Cells," *Ann. New York Acad. Sci.* 660:136–153 (1992).

*Primary Examiner*—Prema Mertz
*Attorney, Agent, or Firm*—Sterne, Kessler, Goldstein & Fox P.L.L.C.

[57] ABSTRACT

Process and medium for the transfection of higher eukaryotic cells with DNA/polycation complexes, wherein a medium is used which contains ethyleneglycol and/or glycerol. The medium may also contain a substance which prevents the acidification of the endosomes, and/or a lower alcohol such as ethanol. The process is particularly suitable for the transfection of primary cells such as fibroblasts. Stably transformed cells can be obtained thereby, e.g. tumour cells for use as tumour vaccines.

49 Claims, 17 Drawing Sheets

METHOD FOR INTRODUCING NUCLEIC ACIDS INTO HIGHER EUKARYOTIC CELLS

CROSS REFERENCE TO RELATED APPLICATION

This is a 371 of PCT/EP95/01969 filed May 24, 1995, now WO 95/33061.

The present invention relates to a process for introducing nucleic acid into higher eukaryotic cells.

There is a need for an efficient system for introducing nucleic acid into living cells particularly in the field of gene therapy. This involves locking genes into cells in order to achieve in vivo synthesis of therapeutically active gene products.

Standard transfection methods used, inter alia, calcium phosphate, cationic lipides or liposomes, whilst in order to improve the transfection efficiency of some of these methods, it has been proposed to carry out osmotic shock treatment of the cells with glycerol or with dimethylsulphoxide (Chen and Okayama, 1988; Parker and Stark, 1979; Okada and Rechsteiner, 1982).

The technologies which are currently most advanced for the use of nucleic acids in the field of gene therapy make use of retroviral systems to transfer genes into the cell (Wilson et al., 1990; Kasid et al., 1990).

Alternative strategies for gene transfer are based on mechanisms which the cell uses for the transportation of macromolecules. One example of this is the introduction of genes into the cell by the route of receptor-mediated endocytosis (e.g. Wu and Wu, 1987, Wagner et al., 1990, and EP-A1 0388 758).

For gene transfer with DNA/polycation-complexes by means of receptor-mediated endocytosis, an improvement has been proposed which envisages using components on the basis of their ability to release the contents of endosomes, e.g. adenoviruses or fusogenic peptides. The use of the endosomolytic components causes an increase in the efficiency of gene transfer by avoiding breakdown of the DNA complexes internalised in the cell in the lysosomes (Curiel et al., 1991; Curiel et al., 1992a; Zatloukal et al., 1992; Cotten et al., 1992; Wagner et al., 1992; Curiel et al., 1992b; Wo 93/07283). It has been proposed, inter alia, to modify the adenoviruses by binding to polylysine. The adenovirus-polylysine conjugates may be complexed with DNA together with conjugates of transferrin-polylysine, thereby producing ternary transferrin-polylysine/adenovirus-polylysine/DNA-complexes (Wagner et al., 1992). The complexes bind to transferrin and adenovirus receptors on the target cells. After the endocytosis the adenovirus causes the endosomes to break open, resulting in the release of the material from the endosome into the cytoplasm. This technique is more reliable than conventional viral techniques (Cotton et al., 1992).

The aim of the present invention was to provide a process for introducing nucleic acid complexed with polycations into the cell, which constitutes a further improvement in terms of the simplicity of the method and reliability thereof.

The objective was achieved by a means of a process for introducing nucleic acids/polycation complexes into higher eukaryotic cells in which the complexes are placed on the cells in the presence of ethyleneglycol and/or glycerol.

Unlike the treatments with glycerol or dimethylsulphoxide, which are proposed for the calcium phosphate precipitation or DEAE-Dextran method, carried out as an after-treatment subsequent to the introduction of the transfection components, thereby inducing the desired osmotic shock, in the process according to the invention, the polyhydric alcohol is present in the medium throughout the entire transfection time. The polyhydric alcohol is conveniently present as a component of the transfection medium. In the light of the results of the experiments carried out within the scope of the present invention, it can be assumed that the polyhydric alcohol has no osmotic activity but triggers another mechanism.

The optimum concentration of glycerol and/or ethyleneglycol depends on various factors particularly the cell type; it can be determined by titration experiments. Within the scope of the present invention, as a result of such titrations, a concentration of about 8 to 15% (v/v), especially about 8 to 13%, based on the transfection medium, has proved favourable.

In addition to glycerol and/or ethyleneglycol, substances which prevent acidification of the endosomes and hence their conversion into secondary lysosomes (Seglen, 1983) may be added to the medium. These include the compounds known as "lysosomatropic substances". Examples of this group of compounds are chloroquine, monensin, nigericin, ammonium chloride and methylamine.

Preferably, within the scope of the present invention, chloroquine is used in a concentration of about 10 to about 300 $\mu$M, particularly 100 $\mu$M.

Another preferred example of this group of substances is bafilomycin A1, a specific inhibitor of the vacuolar proton pump (Bowman et al., 1988; Yoshimori et al., 1991), which is used in concentrations of about 10 nM to about 1 $\mu$M, particularly about 200 nM.

The choice of these substances and their concentration depend on the type of cell to be treated; these parameters can be determined in preliminary tests to investigate whether various concentrations of the substances in question are able to bring about an increase in expression or are toxic.

Another group of substances which are capable of enhancing the activity of glycerol and/or ethyleneglycol are the lower monohydric alcohols, particularly ethanol.

Ethanol is added in non-toxic concentrations (e.g. up to 3%), particularly in a concentration of from 1 to 1.5%.

Nucleic acids/polycation complexes are known in the art; as regards the composition, the qualitative and quantitative demands made of the complex components and regarding the manufacture of the complexes, reference is made to WO 93/07283: The DNA and RNA molecules, especially therapeutically active nucleic acid molecules, are defined by their particular application; there are no restrictions in terms of their sequence; with regard to the size of the molecules, they may be used for a wide range. Suitable polycations include homologous organic polycations such as polylysine, polyarginine, polyornithine or heterologous polycations having two or more different positively charged amino acids, whilst these polycations may have different chain lengths, as well as non-peptidic synthetic polycations such as polyethylenimine. The polycations used may also be spheroid polycations, which have become known as "Starburst dendrimers" (Haensler and Szoka, 1993). Natural DNA-binding proteins of a polycationic nature such as histones or protamines or analogues or fragments thereof as well as spermine or spermidines are also suitable. The polycations may optionally be modified, e.g. by lipophilic groupings such as hydrocarbon groupings with a similarity to natural lipids (e.g. fatty acids, cholesterol), thereby increasing the affinity of the complexes for the cell membrane. Another possible method of modification consists in hydrophilic groupings which are suitable for increasing the specificity of the complexes for the target cells. Examples of such groupings include sugars, such as lactose, maltose, galactose, and polyethyleneglycol.

Preferably, within the scope of the present invention, polylysine is used as the polycation.

If desired, the polycation, or a proportion thereof, is conjugated with an internalising factor for the target cells. The term "internalising factors" refers to ligands or fragments thereof which are internalised after binding to the cells by endocytosis, preferably receptor-mediated endocytosis, or factors the binding/internalising of which is effected by fusion with cell membrane elements. Examples of suitable internalising factors are described in WO 93/07283. The use of a ligand is particularly advantageous when the cell type to be transfected expresses receptors which internalise well, i.e. receptors which are "active".

One internalising factor which is preferably used within the scope of the present invention is transferrin.

The question of whether the use of an internalising factor is necessary or advisable can easily be answered by comparative tests, by investigating whether and to what extent the presence of an internalising factor conjugate brings about an increase in gene expression under otherwise identical conditions.

Preferably, the transfection complexes are prepared by first combining the DNA with a partial amount of polycation (and/or internalising factor/polycation conjugate), whereby a certain pre-condensation of the DNA is brought about, after which the majority of the polycation and/or internalising factors/polycation conjugate, e.g. transferrin/polylysine, is added.

Preferably, the polycation, e.g. polylysine, or the conjugate of polycation and internalising factor, e.g. transferrin/polylysine, or a mixture thereof, is used in excess, so that the DNA complexes are electropositive. The experiments carried out within the scope of the present invention have shown that, depending on the type of cell, a molar excess of positive charge (e.g. in the form of polylysine) of about 25% up to about a two-fold excess gives good results.

The process according to the invention is particularly advantageous when applied to primary cells such as fibroblasts.

According to another aspect the invention relates to a process for preparing cells which express a heterologous peptide from a stably transfected DNA molecule. Following the transfection of the cells in the presence of glycerol and/or ethyleneglycol optionally with the addition of lysosomatropic substance and/or a lower alcohol, with a complex of a DNA molecule coding for the heterologous polypeptide and a polycation which is optionally wholly or partially conjugated with an internalising factor, the cells are cultured, stable cell clones are selected and possibly cell lines are established therefrom.

The selection of stable cell clones and the establishing of cell lines are carried out by conventional methods; such methods can be found in the relevant manuals e.g. Current Protocols in Molecular Biology, F. M. Ausubel et al. (Ed.), Vol. 1, Supplement 14, 1987, 9.5.

This application may be considered, for example, for the transfection of eukaryotic cells in order to produce recombinant polypeptides or to produce tumour vaccines.

The cell lines obtained in the case of tumour cells, which express, from an integrated gene, an immunostimulant polypeptide such as cytokine, and/or one or more tumour antigens, are suitable for use as tumour vaccines.

According to another aspect, the invention relates to a transfection medium, containing as its active component complexes of nucleic acid and of a polycation which is optionally wholly or partially conjugated with an internalising factor, as well as glycerol and/or ethyleneglycol, and optionally an added amount of lysosomatropic substance and/or a lower alcohol. In addition to the transfection components, the medium contains the usual nutrients and additives adapted to the particular cell type, e.g. in the form of commercially obtainable cell culture media.

Within the scope of the present invention, the application of the present invention to cells of various cell lines, to primary cells and to the preparation of stable cell clones which express a heterologous polypeptides has been demonstrated.

Figure 1:
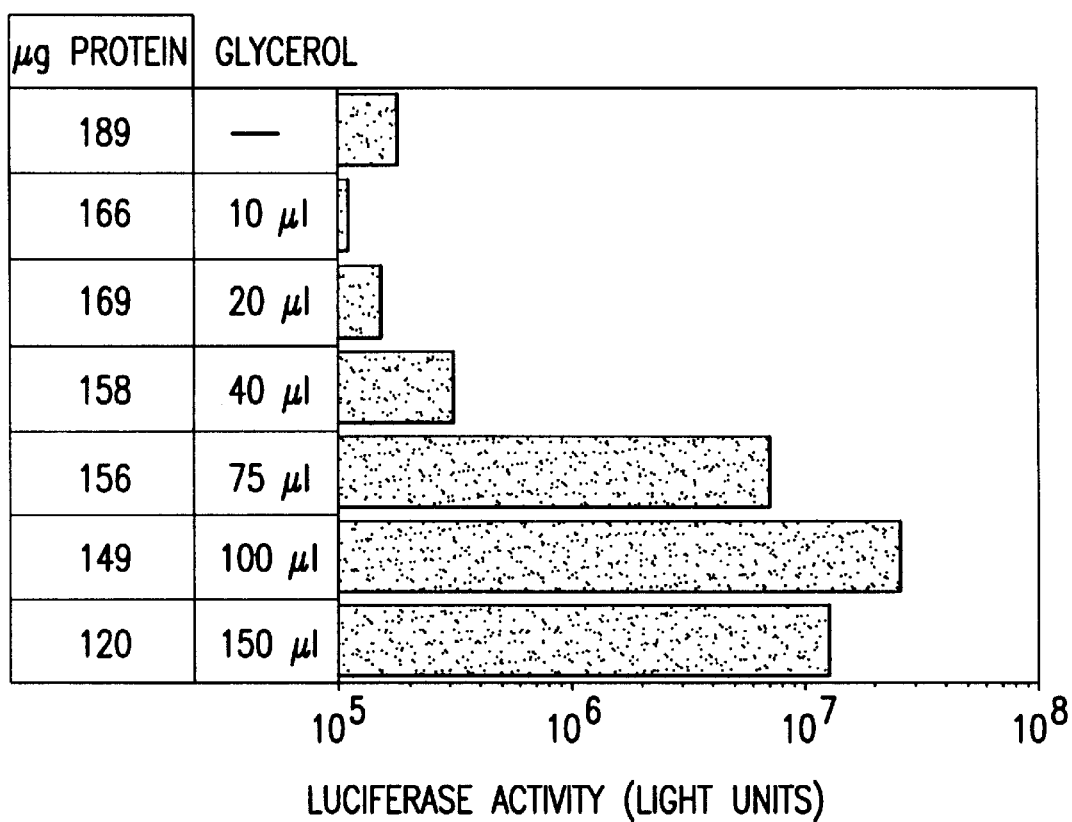
FIG. 1: Titration of glycerol in the transfection of human melanoma cells

The embodiments by way of example illustrate the invention; unless otherwise stated, the following materials and methods were used (in some examples, streptavidinylated polylysine was used instead of polylysine; this difference had no noticeable effect in the efficiency of gene expression compared with non-modified polylysine):

i) Plasmid-DNA

The construction of the plasmid pCMVL is described in WO 93/07283, that of the plasmid pGShIL2-tet is described in WO 94/21808.

The plasmid pRSVneo was described by Gorman, 1985, ii) Transferrin-polylysine-conjugates The method described by Wagner et al., 1991, was used to synthesise conjugates of transferrin (Tf) and polylysine (pL) with a chain length of 290 lysine groups or 250 lysine groups (TfpL290 and TfpL250, respectively). The molar ratio of transferrin to polylysine was about 1:1.2.

iii) Streptavidin-polylysine-conjugates (StpL)

The conjugates were prepared as described in WO 93/07283, using polylysine 250.

iv) Human melanoma cells H225

Primary human melanoma cells were isolated from surgically removed melanomas. The tumours were cut up into small fragments mechanically (with tweezers and a surgical blade) in the presence of RPMI 1640 culture medium, containing 5% FCS, 2 mM glutamine and antibiotics. The tissue fragments were then carefully forced through a metal screen using the plunger of a syringe. Then the material was washed several times by centrifuging and resuspension and the cells released were seeded out in T25-culture flasks. The cells were transfected in a quantity of 100,000 cells per well.

v) Human fibroblasts

After surgical removal, skin biopsies were placed in 4° C. DMEM, containing 10% FCS, 2 mM glutamine and gentamycin. The biopsies were carefully cut up in a tissue culture apparatus using tweezers and the surgical blade in a laminar air current in sterile 6 cm plastic dishes. Then 3 ml DMEM, containing 20% FCS, 2 mM glutamine and antibiotics, was added and the culture was placed in an incubator at 37° C. After ten days the medium was exchanged for DMEM containing 10% of FCS. Then the medium was changed a further two times a week. Four weeks after the start of the culture, the cells which had grown out of the tissue fragments were trypsinised and plated out in new culture dishes for transfection.

An alternative preferred method consisted of transferring the fragments of skin into fresh medium after cutting them up and washing them once or twice with medium as required. 5 to 10 pieces of tissue were placed in a T25-tissue culture flask, the surface of which had been wetted with DMEM plus 10% FCS, and were then uniformly distributed, after which the flask was rotated. This caused the biopsies to hang down ("hanging drop configuration"; this method was described by Jones, 1989). After 1 to 3 hours in the incubator the flasks were then rotated again and filled with 1 to 2 ml of medium. Any fixed biopsies were topped up to 5 ml after 24 hours; otherwise the process was repeated. After 6 to 10 days the first fibroblast grew out and from this time on the medium was changed once a week. As soon as the cells were confluent they were passaged into a T75-flask.

vi) Cell lines

The following cell lines were obtained from ATCC: NIH 3T3 (ATCC CRL 1658), A549 (ATCC CCL 185) and TIB 73 (ATCC BNL CL.2).

vii) Luciferase-assay

The preparation of cell extracts, the standardisation of the protein content and the measurement of the luciferase activity were carried out as described in WO 93/07283, by harvesting the cells in 250 mM TRIS pH 7.3, 0.5% Triton X-100 and measuring the luciferase activity of one aliquot of the supernatant.

viii) Interleukin-2-assay

The expression of IL-2 was measured in the cell supernatant with a commercially obtainable ELISA (Bender MedSystems, Vienna).

ix) Chemicals

Glycerol, ethyleneglycol, diethyleneglycol, polyethyleneglycol (PEG) 1000 and 6000 were obtained from Fluka (Buchs, Switzerland), threitol was obtained from Aldrich (Vienna, Austria). (The concentration of commercially available glycerol is about 87%. 10% (v/v) thus indicates, for example, the addition of 200 µl of the starting preparation to a final volume of transfection medium of 2 ml.)

EXAMPLE 1

Figure 2:
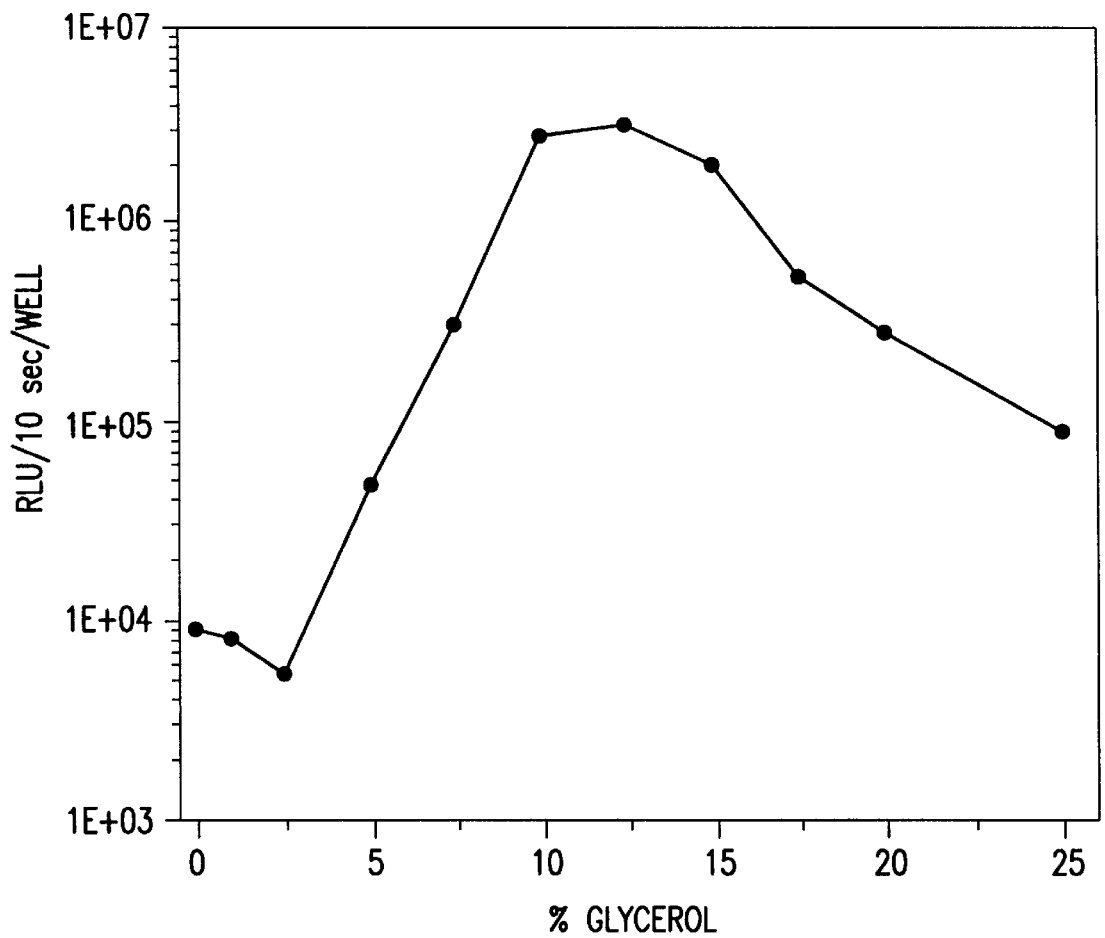
FIG. 2: Titration of glycerol in the transfection of human melanoma cells
Figure 3:
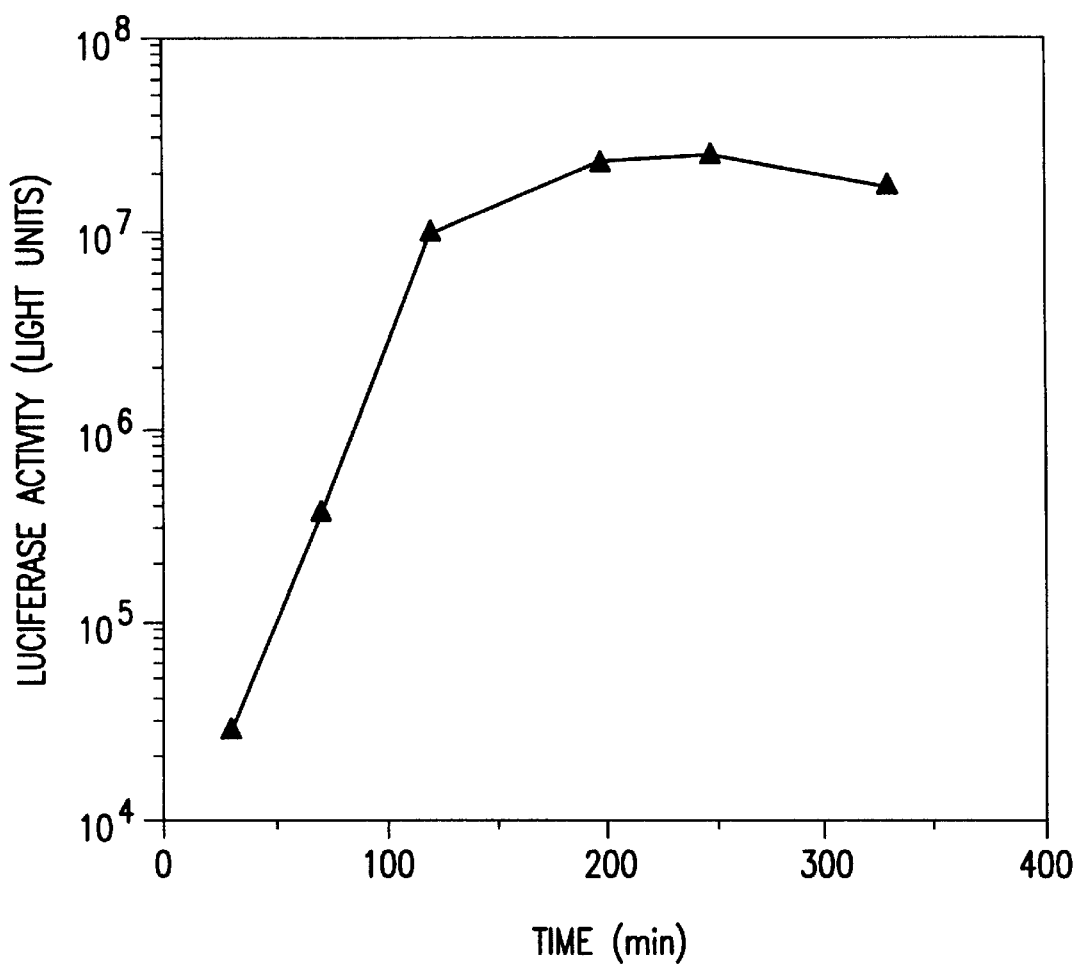
FIG. 3: Optimisation of the transfection conditions—passage of time

Titration of glycerol in the transfection of human melanoma cells a) 0.4 µg of streptavidin-modified polylysine was diluted in 75 µl of HBS and incubated for 30 minutes after the addition of 3 µg of pCMVL in 75 µl of HBS. Then 3 µg of transferrin-polylysine (TfpL290) in 75 µl HBS was added and incubation was continued for a further 30 minutes. After the addition of the amount of glycerol as specified in FIG. 1., 700 µl of medium (RPMI 1640 plus FCS, 2mM L-Glu, 1 mM sodium pyruvate, antibiotics) was added and the mixture was pipetted onto the cells. The transfection medium was suction filtered after 4 hours and the cells were mixed with fresh medium (without transfection components). The harvesting of the cells and measurement of the luciferase activity were carried out after 24 hours using standard procedures. The results of the transfections are given in FIG. 1 (the protein quantity of the cell lysate determined according to Bradford is given). Increasing quantities of glycerol in the medium caused an increase in the luciferase activity up to the concentration of 10% (1.15M). At a glycerol content of 15% a drop in expression was observed.

b) As in a), 100,000 H225-cells per well were transfected with complexes consisting of 1.5 µg of pCMVL, 0.2 µg of pL and 1.5 µg of TfpL in the presence of glycerol in concentrations (v/v) specified in FIG. 2. It was found that 10% glycerol (1.15M) gave the best results; a concentration of less than 4% did not bring about any increase in reporter gene expression, whereas concentrations of 15% or more were toxic to the H225 cells. The luciferase values are the averages of double measurements and represent relative light units per mg of protein and 10 seconds.

c) In order to optimise the transfection conditions, a time experiment was carried out in which the transfections were carried out as in b) in the presence of 10% (v/v) glycerol. After the time specified in FIG. 3 the medium was replaced. It was found that the highest expression levels were obtained when the cells had been incubated for 3 to 4 hours with the complexes and glycerol.

EXAMPLE 2

Figure 4:
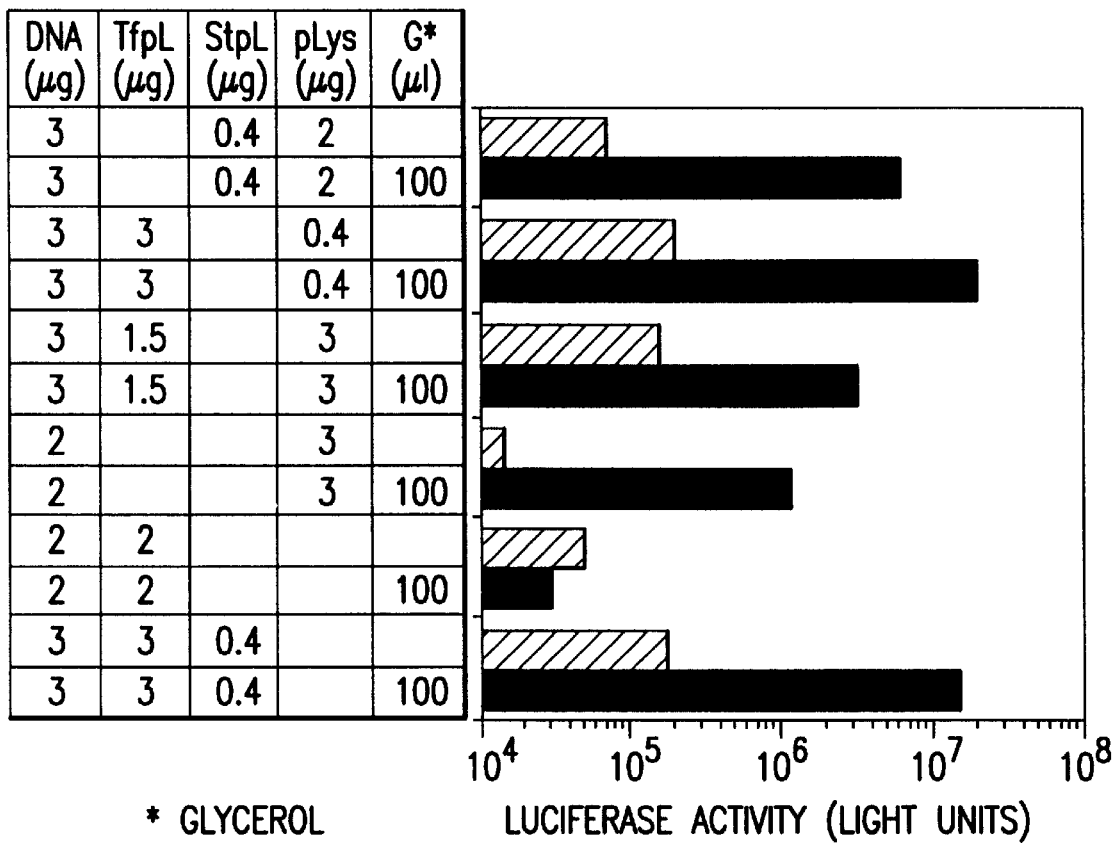
FIG. 4: Investigation of efficiency of various gene transfer complexes for the transfection of primary melanoma cells in the presence of glycerol
Figure 5:
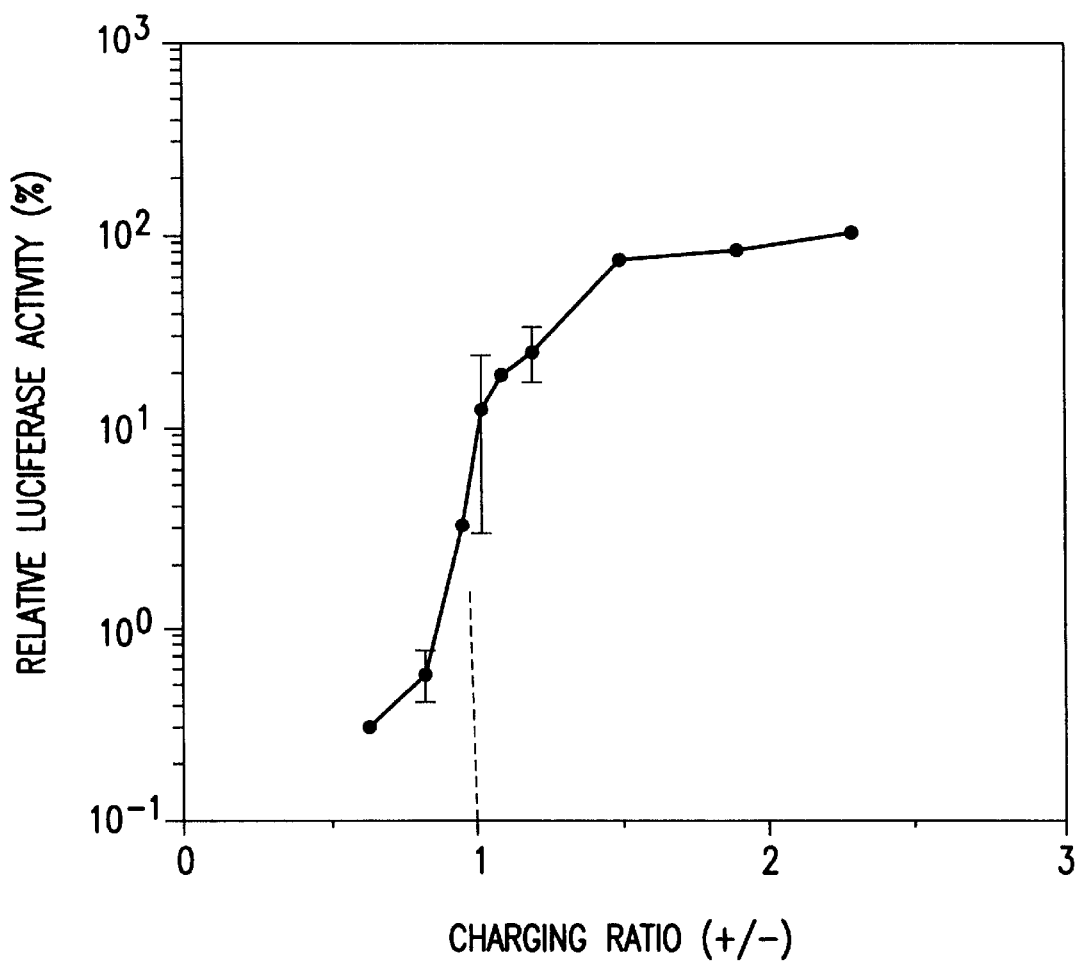
FIG. 5: Titration of the charging of the complex components
Figure 6:
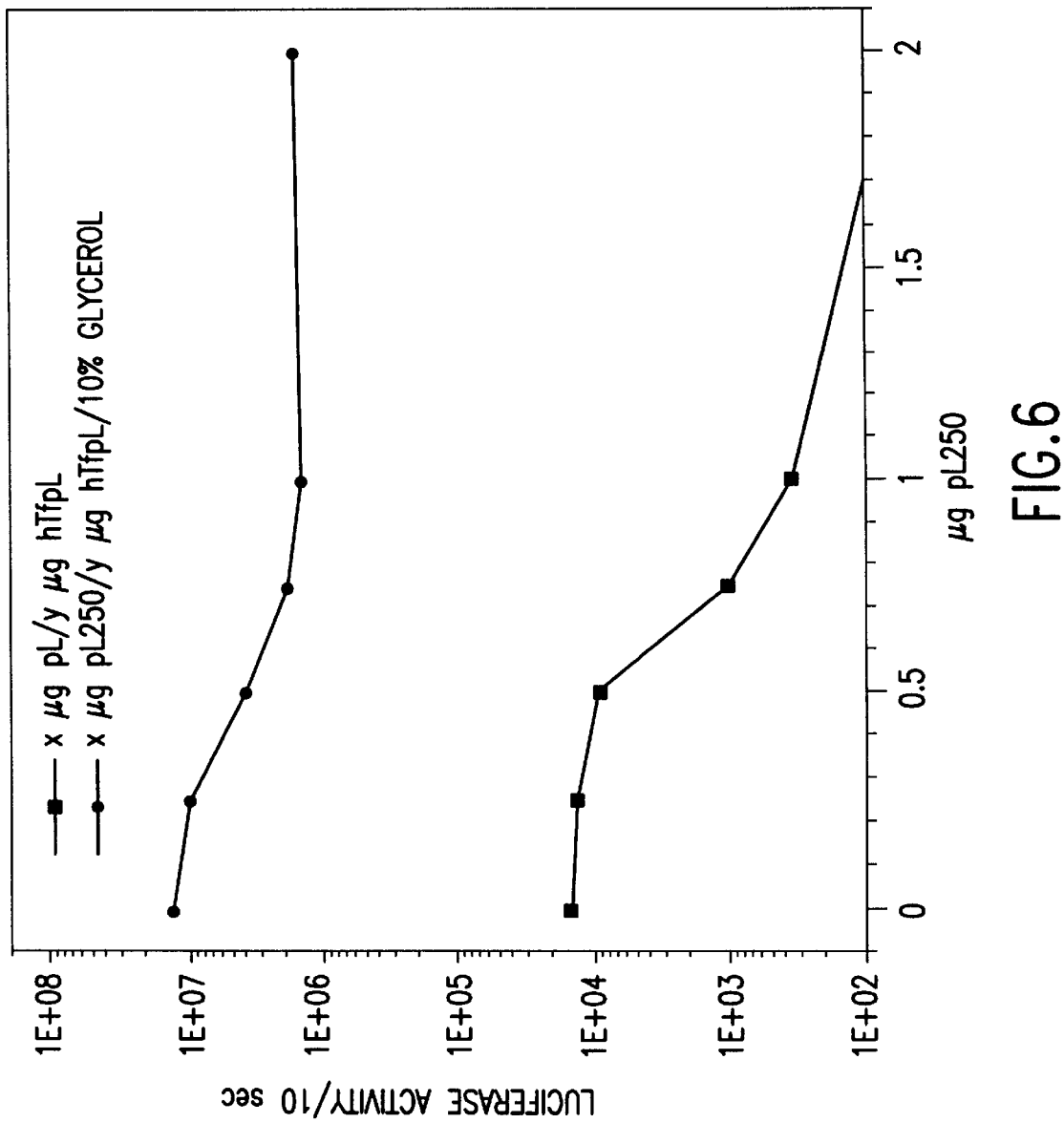
FIG. 6: Replacement of transferrin-polylysine by polylysine in positively charged complexes

Investigation into the efficiency of various gene transfer complexes for the transfection of primary melanoma cells in the presence of glycerol a) 0.4 µl of StpL or pL300 in 75 µl of HBS were incubated for 30 minutes with 3 µg of pCMVL in 75 µl of HBS, then 3 µg of TfpL290 or pL in 75 µl of HBS were added and incubation was continued for a further 30 minutes. DNA/pL- and DNA/TfpL-complexes were prepared by mixing the components in 75 µl HBS and incubating for 30 minutes. Electro-positive DNA/TfpL/pL-complexes were prepared by incubating 3 µg DNA and 1.5 µg TfpL290 for 30 minutes and then adding 3 µg of pL. After the addition of glycerol and medium, the complexes were placed for 4 hours on the primary melanoma cells designated H225 then the medium was replaced by fresh medium. The harvesting of the cells and the measurement of the luciferase activity were carried out after 24 hours. The results of the transfections are shown in FIG. 4: The cells which were transfected in the presence of 10% glycerol (the concentrations specified in this Example and the following Examples refer to the total volume), showed a significantly higher expression than without glycerol, with one exception.

b) In another experiment on the titration of the charge, H225-cells as described in the previous Examples were transfected with complexes of 1.5 μg of pCMVL (4.5 nmol negative charges), 0.2 μg of pL and increasing amounts of TfpL. FIG. 5 shows the relative expression levels as a function of the charging ratio (mol positive charges/mol negative charges). It was found that the efficiency of gene transfer correlates with the total charge of the complex; an at least slight excess of positive charges proved necessary for efficient gene transfer.

c) H225-cells were transfected in the presence or absence of 10% glycerol with complexes consisting of 1.5 μg of DNA and with mixtures of TfpL/pL which give a charging ratio (plus/minus) of 1.5. The results are shown in FIG. 6; it is apparent that TfpL can be replaced by pL in positively charged complexes without substantially reducing the reporter gene expression.

EXAMPLE 3

Figure 7:
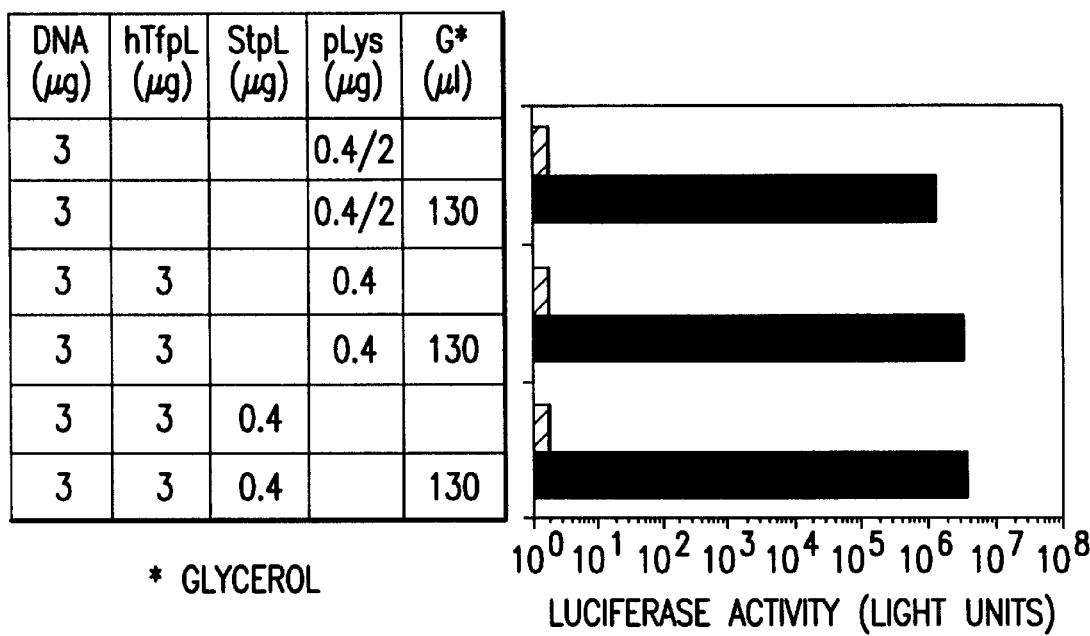
FIG. 7: Transfection of primary human fibroblasts with a luciferase reporter plasmid in the presence of glycerol

Transfection of primary human fibroblasts in the presence of glycerol a) Transfection with a luciferase reporter plasmid 0.4 μg of pL or StpL in 75 AL of HBS were incubated for 30 minutes with 3 μg of pCMVL in 75 μl of HBS, then 3 μg of TfpL290 or 2 μg of pL in 75 μl of HBS were added and incubation was continued for a further 30 minutes. After the addition of medium and 13% glycerol to the complexes the transfection medium was placed for 4 hours on the cells (45,000 cells per well). The harvesting of the cells and the measurement of the luciferase activity were carried out after 24 hours. The results of the transfections are given in FIG. 7.

b) Transfection with a plasmid coding for IL-2

Figure 8:
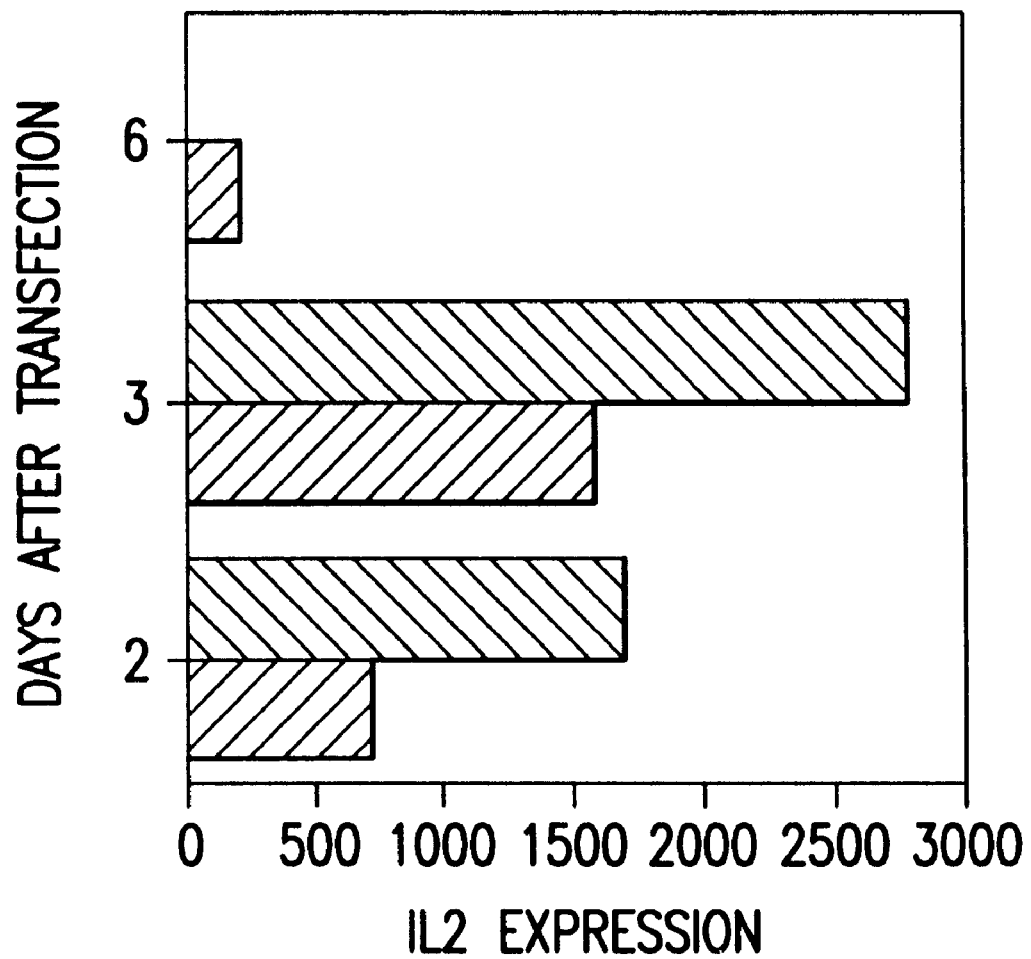
FIG. 8: Transfection of primary human fibroblasts with a plasmid coding for IL-2 in the presence of glycerol

0.9 μg of polylysine in 75 μl HES were incubated for 30 minutes with 6 μg of pCMVL in 75 μl HBS, then 6 μg of TfpL250 in 75 μl of HBS were added and incubation was continued for a further 30 minutes. After the addition of medium and 10 or 15% of glycerol, the transfection complexes were placed for 4 hours on the cells (200,000 cells/6 cm culture dish). Then the medium was replaced with fresh medium and subsequently changed daily and the IL-2-expressions was measured in the supernatant by means of ELISA in accordance with the manufacturer's instructions. The results of the transfections are shown in FIG. 8, the darker bars indicating the expression in the presence of 15% glycerol whilst the lighter bars show the expression in the presence of 10% glycerol.

EXAMPLE 4

Figure 9:
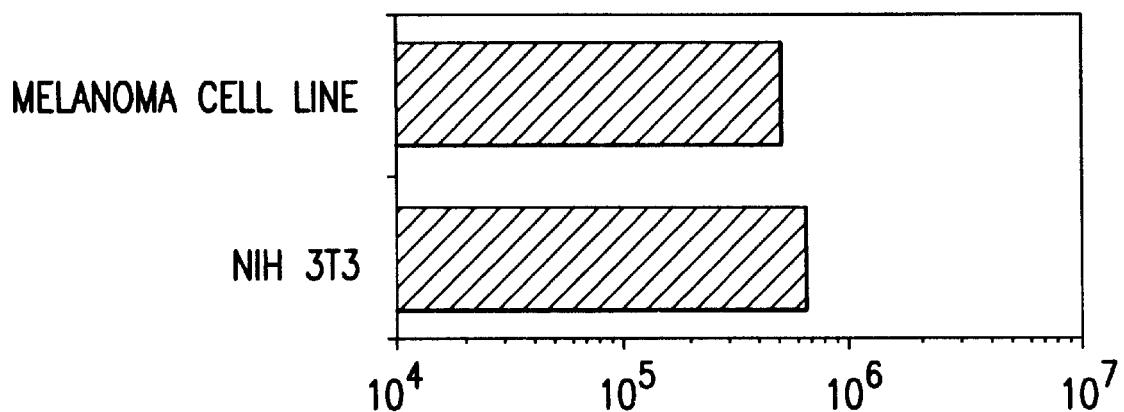
FIG. 9: Transfection of the cell line NIH 3T3 and a melanoma cell line in the presence of glycerol

Transfection of cell lines in the presence of glycerol a) NIH 3T3-cells Cells of a melanoma cell line The transfection complexes were prepared from 3 μg pCMVL, 3 μg TfpL and 0.4 μg StpL as described in the preceding Examples. After the addition of 75 μl of glycerol the mixture was made up to 1 ml with DMEM-medium. The transfection medium was added to 50,000 cells of the cell line NIH 3T3 (ATCC CRL 1658) or a cell line obtained from melanoma cells which had been subjected to a high number of passages (50,000 cells per well). After 4 hours the transfection medium was supplemented with fresh medium as described in the preceding Examples. The results of the transfections are shown in FIG. 9.

b) Lung cancer cells (cell line A549)

i) Transfection in the presence of 15% glycerol

Figure 10:
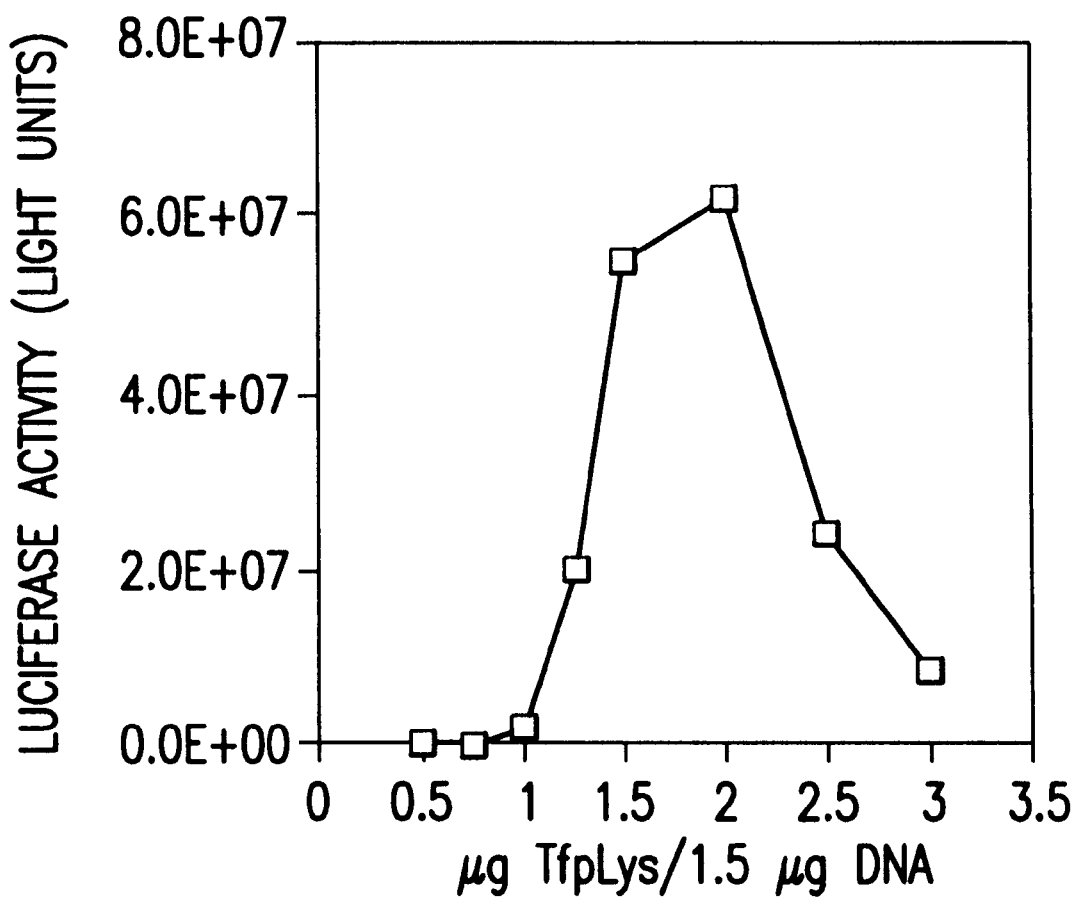
FIG. 10: Transfection of A549-cells in the presence of 15% glycerol

The transfection complexes were prepared from 1.5 μg pCMVL-DNA and the quantities of TfpL250 specified in FIG. 10, as described in the preceding Examples. After the addition of medium (DMEM/10% FCS) and glycerol (final concentration 15%) the complexes were placed for 4 hours on 100,000 cells per well in a 6-well dish. Then the medium was changed and after 24 hours the luciferase activity was measured. The results of the test are given in FIG. 10.

ii) Transfection in the presence of different amounts of glycerol

Figure 11:
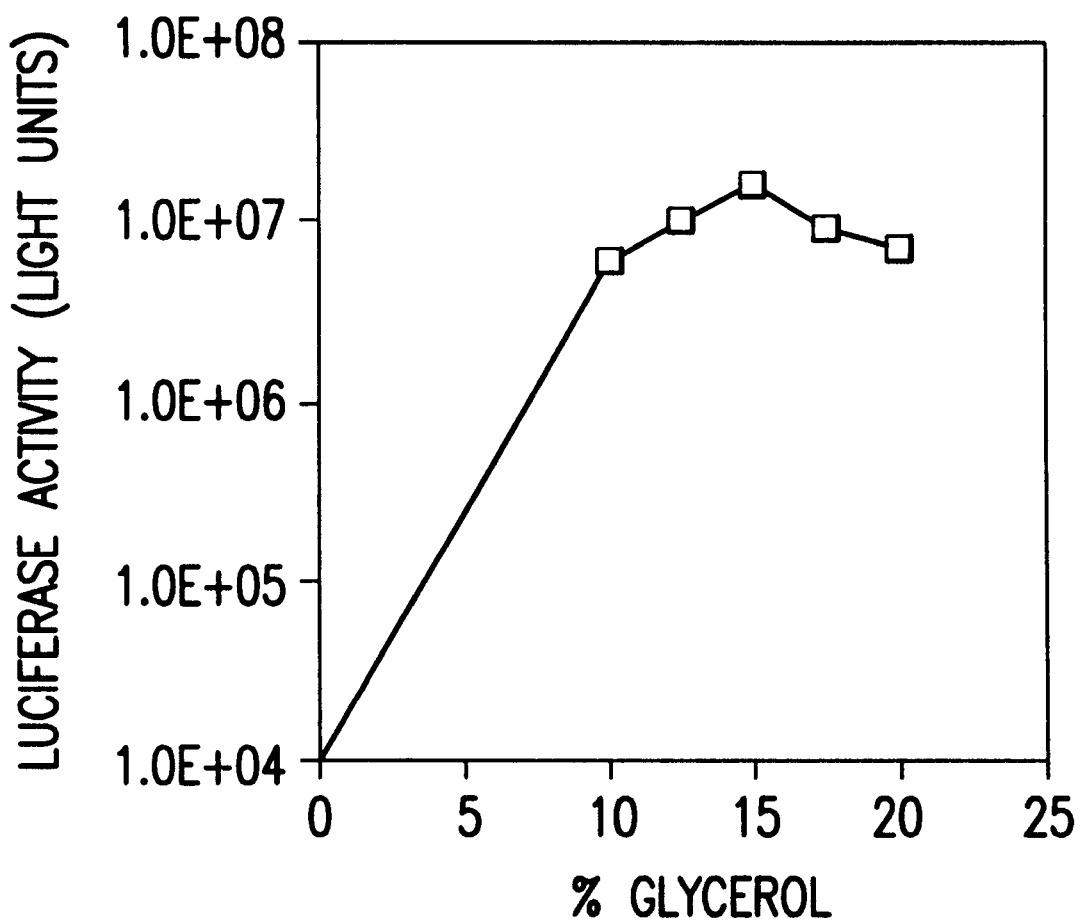
FIG. 11: Transfection of A549-cells in the presence of different amounts of glycerol

The same procedure was used as in the test plan as described in i), the transfection complexes being prepared from 1.5 μg of PCMVL-DNA and 1.5 μg TfpL250. After the addition of medium and various amounts of glycerol and the concentrations specified in FIG. 11, the cells were treated as stated in i) and the luciferase activity was measured (FIG. 11).

c) HeLa-cells BNL CL.2-cells

Figure 12:
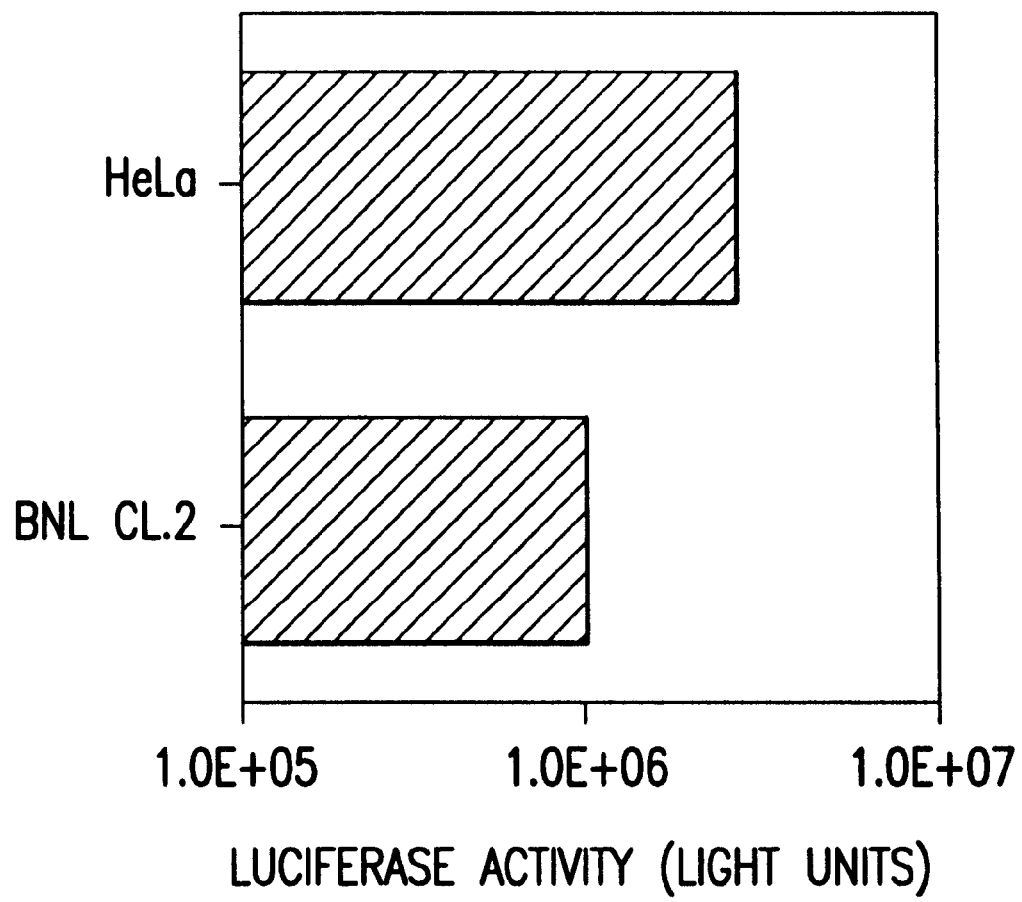
FIG. 12: Transfection of HeLa-cells and BNL CL.2-cells in the presence of glycerol

The transfection complexes were prepared from 1.5 μg pCMVL-DNA and 1.5 μg TfpL290 as described in the preceding Examples. For the transfection of the HeLa-cells DMEM-medium with 10% glycerol was used whilst for the transfection of the BNL CL.2-cells high glucose DMEM-medium (plus 10% FCS, glutamine, antibiotics) with 15% glycerol was used. After 4 hours the mixtures were supplemented with fresh medium and after 24 hours the luciferase activity was measured; the results are shown in FIG. 12.

EXAMPLE 5

Investigation of the influence of other substances as replacements for glycerol a) Transfection of primary human melanoma cells in the presence of glycerol or threitol The transfection complexes in this Example were prepared as described in Example 2. Before the transfection, 10% glycerol or 20% threitol (50%) were added to the medium. The transfections were carried out per 100,000 cells as described in Example 2.

Figure 13:
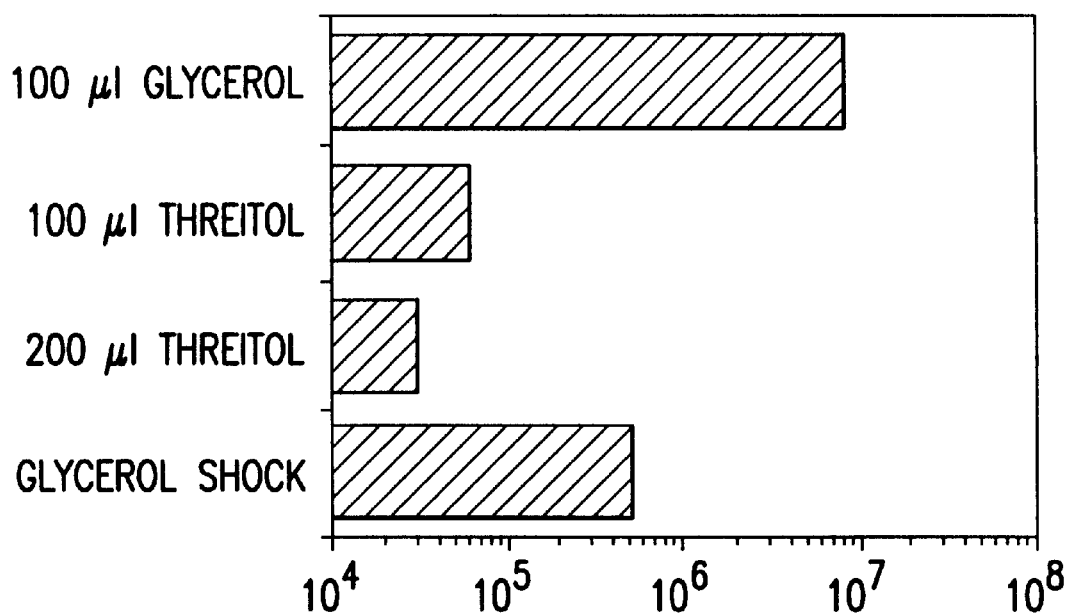
FIG. 13: Transfection of primary human melanoma cells in the presence of glycerol or threitol
Figure 14:
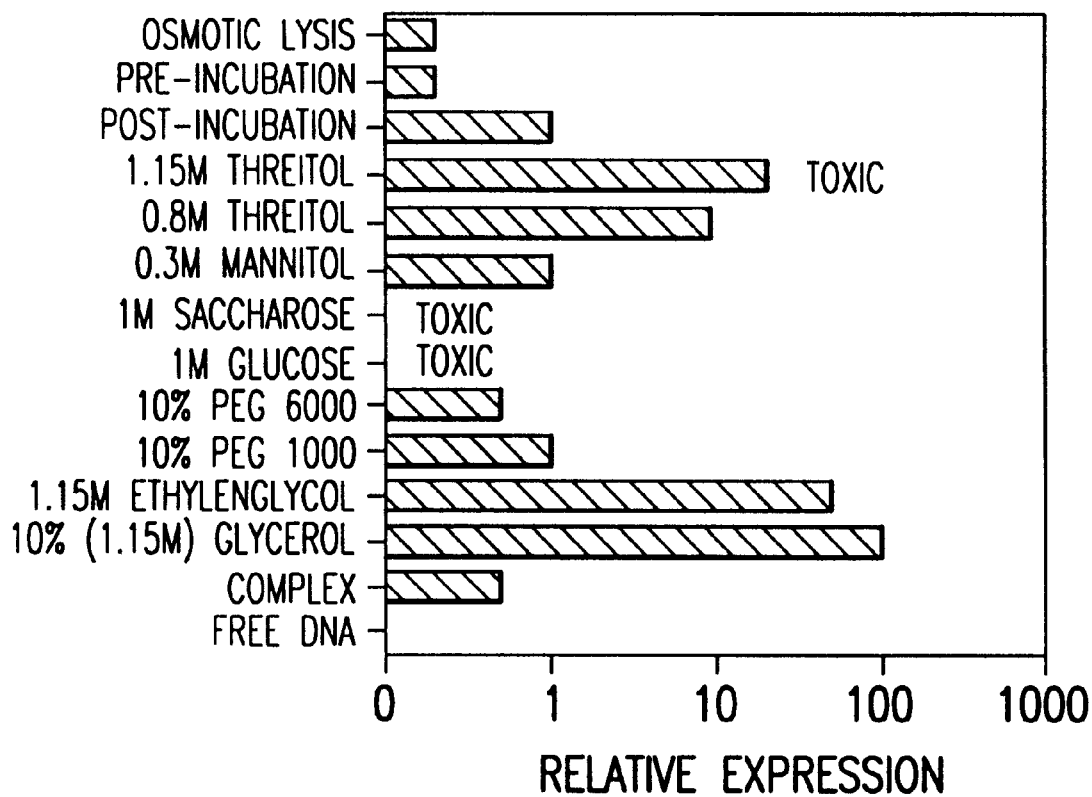
FIG. 14: Investigation of various substances for their ability to increase gene transfer efficiency

In a parallel experiment, after the 4 hour incubation with the transfection complexes and the suction filtering of the complexes, glycerol was added to the cells in a concentration of 20% for 15 minutes in order to bring about osmotic shock, then the glycerol was suction filtered. The results of the transfections are shown in FIG. 13; the treatment with threitol instead of glycerol during transfection produce significantly worse expression values than with glycerol. It was also found that the shock treatment with glycerol is significantly less efficient than the presence of glycerol throughout the entire duration of the transfection.

b) In this experiment, various substances which are chemically similar to glycerol were investigated for their ability to improve gene transfer efficiency. For this purpose, H225-cells were transfected with complexes consisting of 3 μg of pCMVL, 0.4 μg of pL and 3 μg of TfpL in the presence of the substances specified in FIG. 14 in the concentrations given. The osmotic lysis shown in the top column was carried out using the method described by Okada and Rechsteiner, 1982, with the DNA/TfpL complexes, mixed in hypertonic medium (duration: 3 hours and 20 minutes respectively; medium/0.5M glucose/10% PEG 1000). After the transfection, the cells were washed twice with hypotonic medium (medium/water=6/4) and kept hypotonic for 3 minutes before being further cultured in normal medium (the different length of treatment in hypertonic medium gave identical results and therefore only one value is shown in the Figure; corresponding experiments with BNL CL.2 cells gave similar results). None of the substances used apart from ethyleneglycol, which showed 30 to 50% of the effectiveness of glycerol with the same molarity under the test conditions, proved suitable to increase reporter gene expression substantially. The lower activity of ethyleneglycol could be put down to a toxic effect, at least in part. All the other substances were toxic in a concentration significantly below 1.15M (corresponding to glycerol 10%). The values shown in columns 2 and 3 were obtained by incubating the cells with 10% glycerol before or after transfection; they show that the effect of glycerol is dependent on its presence during transfection; neither pre-treatment nor after-treatment (referred to as pre- and post-incubation in the Figure) with glycerol significantly increased the reporter gene expression.

EXAMPLE 6

Figure 15:
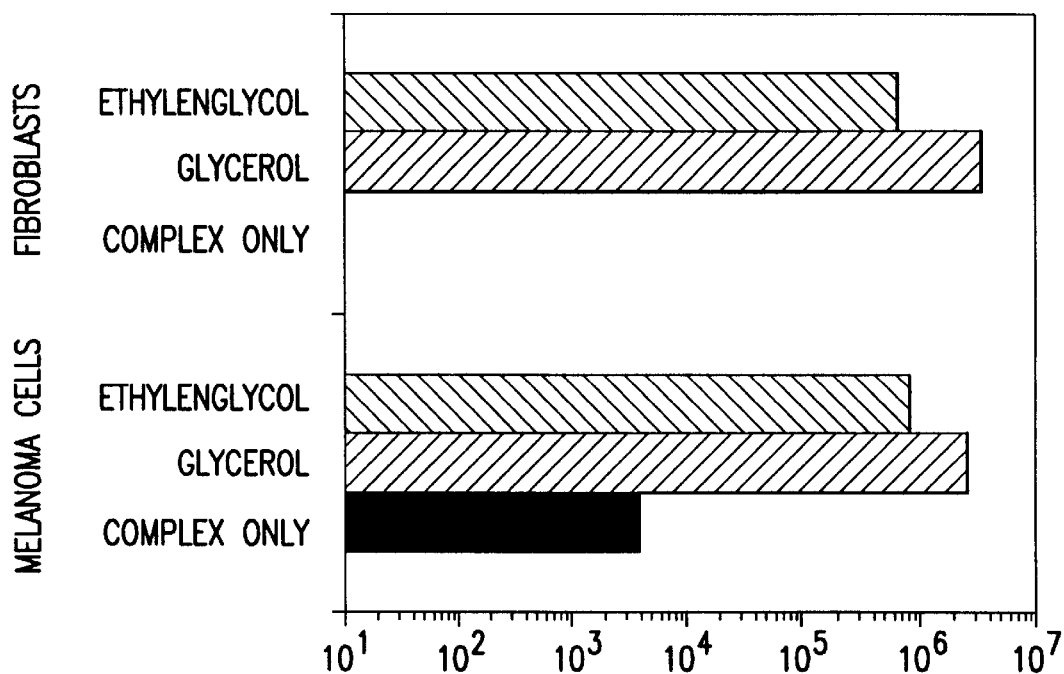
FIG. 15: Transfection of primary melanoma cells or fibroblasts in the presence of glycerol or ethyleneglycol

Transfection of primary melanoma cells or fibroblasts in the presence of glycerol or ethyleneglycol The transfection complexes were prepared as described in the preceding Examples. 10% glycerol or ethyleneglycol were added to the transfection medium before it was applied to the cells. 100,000 melanoma cells or 50,000 fibroblasts were used for each transfection. The results of the transfections are shown in FIG. 15: In the case of the fibroblasts the complex with no additives could not bring about any expression; in the case of melanoma cells the addition of ethyleneglycol or glycerol brought about an increase of about 3 powers of ten. The absolute expression values on addition of the polyhydric alcohols were roughly the same for both cell types.

EXAMPLE 7

Figure 16:
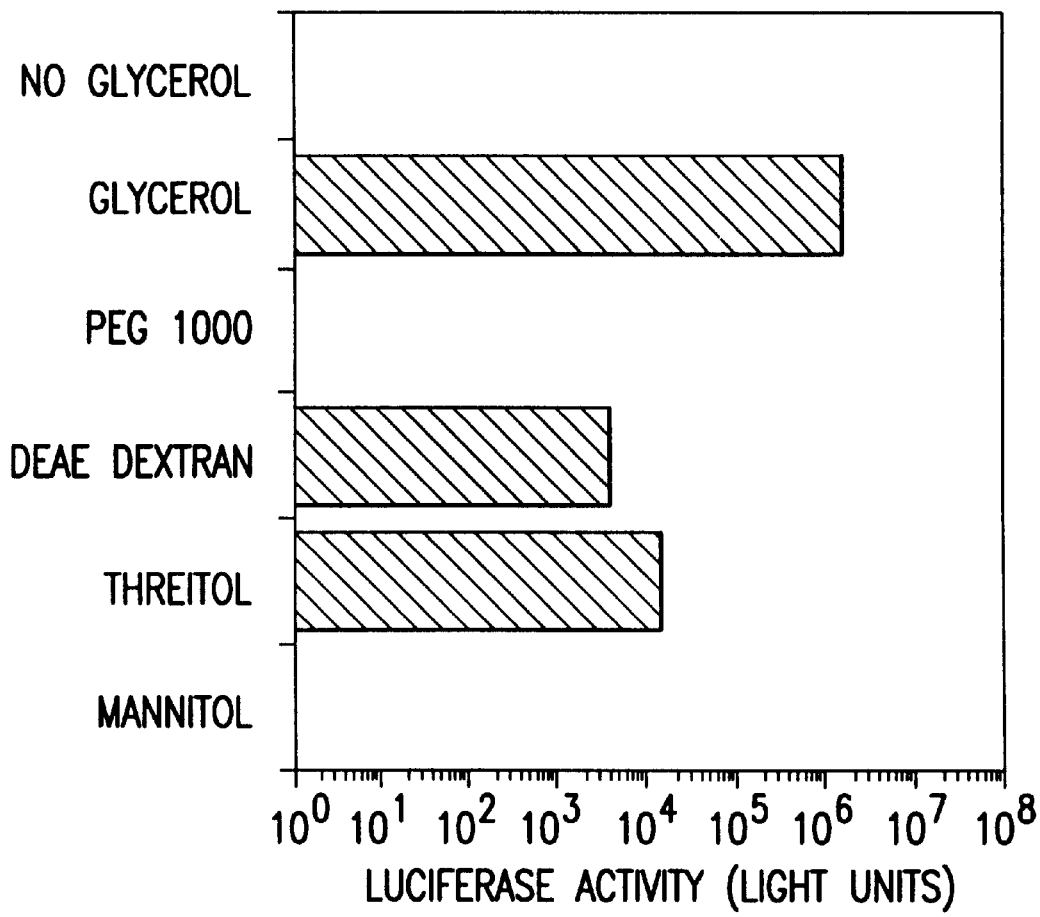
FIG. 16: Transfection of primary fibroblasts in the presence of various polyhydric alcohols or DEAE-dextran

Transfection of primary fibroblasts in the presence of various polyhydric alcohols The transfection complexes in this Example were prepared as described in Example 3. Before the transfection, 13% glycerol, 20% polyethyleneglycol 1,000 (50%), 250 µg/ml DEAE-dextran or mannitol (170 mM) or 20% threitol (50%) were added to the medium; a sample was transfected without any additives whatsoever. The transfections were carried out per 40,000 cells as described in Example 3. The results of the transfections are shown in FIG. 16; it was found that, without the addition of glycerol or if polyethyleneglycol or mannitol was added, there was no expression; the addition of threitol resulted in only slightly better expression compared with the DEAE-dextran method. This result also indicates that the activity of glycerol is not osmotic; if this were the case, the higher-hydric alcohols would also show a similar effect.

EXAMPLE 8

Preparation of stable melanoma cell clones

Figure 17:
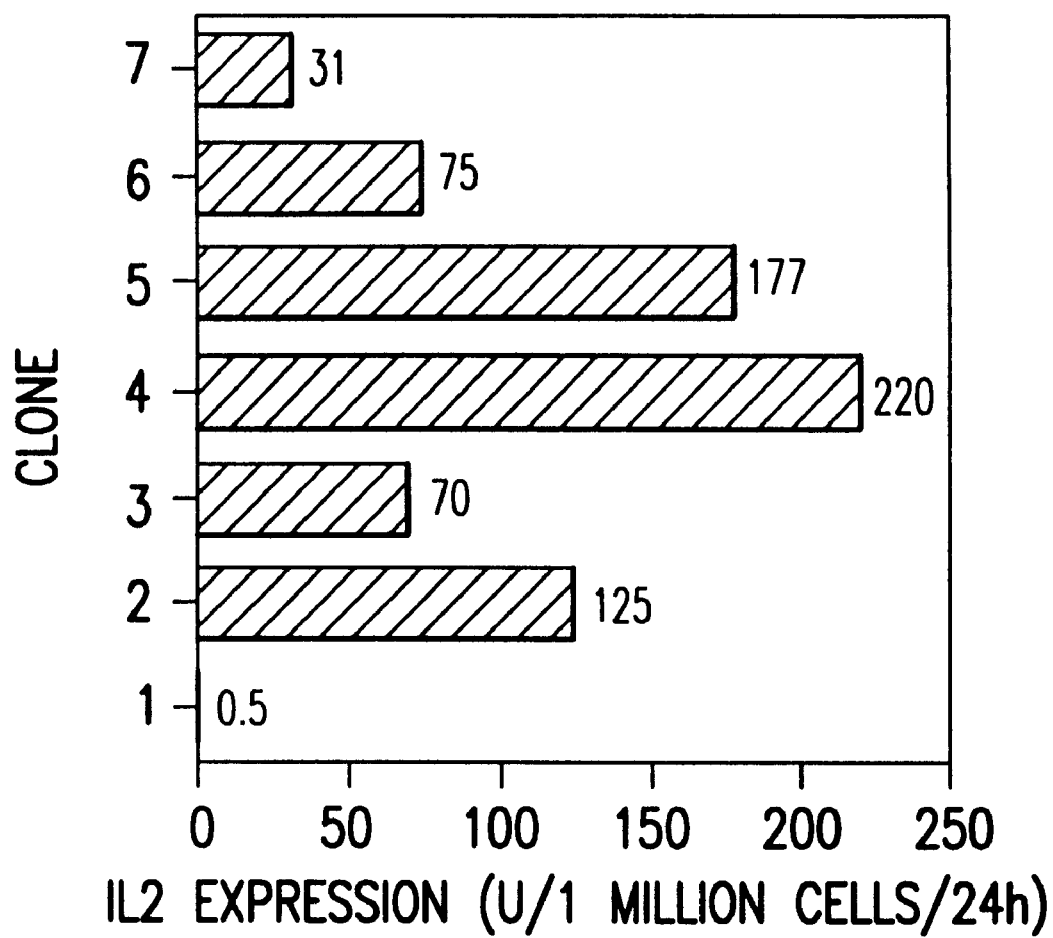
FIG. 17: Preparation of stable melanoma cell clones.

In order to prepare the transfection complexes, first the plasmid pGShIL2-tet linearised with XmnI was mixed with XmnI-linearised plasmid pRSVneo in the ratio 10:1 (6 µg pGShIL2-tet/0.6 µg pRSVneo) in 100 µl HBS. 7.5 µg of TfpL250 in 100 µl of HBS were added and the mixture was incubated for 30 minutes at ambient temperature. The mixture was added to H225-cells (300,000/T25-culture flask; Manufacturer: Nunc) with medium (RPMI 1640, 1 mM sodium pyruvate), containing 10% glycerol. After 4 hours this was replaced by fresh medium. After 60 hours selection was begun by means of medium containing 3 mg/ml of geneticin (G418, Sigma), after 5 days the concentration of G418 was reduced to 1 mg/ml. The cells were passaged in medium containing 1 mg/ml G418. In order to determine the IL-2-expression, 400,000 cells per well were plated out in a 6-well plate. After 24 hours the medium was replaced by 2 ml of fresh medium. After a further 24 hours incubation the IL-2 contained in the supernatant was measured in the ELISA in accordance with the manufacturer's instructions. The number of cells was determined by counting after trypsinisation. The values given in FIG. 17 correspond to IL-2-units per 24 hours per $10^6$ cells.

EXAMPLE 9

Investigation of the influence of other substances and parameters for their ability to bring about an increase in gene transfer efficiency achieved by glycerol In these experiments, the results of which are shown in the Table, the transfections were carried out for the type of cell as described in the preceding Examples; the transfection complexes used had the following composition:

A: 1.5 µg DNA/0.2 µg pL/1.25 µg TfpL

B: 1.5 µg DNA/1.5 µg TfpL

C: 1.5 µg DNA/0.2 µg pL/1 µg pL (pL was added in 2 batches)

D: 1.5 µg DNA/1.2 µg pL

Chloroquine was used in a concentration of 100 µM, bafilomycin µl in a concentration of 200 nM and ethanol in a concentration of 1% or 1.5%. The total volume of transfection medium was 1 ml in each case.

The results of these experiments are shown in the Table; the expression values given refer to the relative light units which were obtained with complex A in the presence of 10% glycerol (=100%). 100% corresponds to $1.5 \times 10^7$ light units per $10^5$ H225-cells, $1.5 \times 10^6$ light units per $10^5$ NIH 3T3-cells, $10^7$ light units per $10^5$ A549-cells or $1.2 \times 10^6$ light units per $10^5$ primary human fibroblasts.

In another experiment (not contained in the Table) the concentration of the complex was increased by reducing the volume of transfection medium from 1 ml from 700 µl (the glycerol concentration was 10% and the ethanol concentration 1.5%). This measure resulted in a five-fold increase in luciferase expression.

TABLE

| Cells | Complex | Glycerol % (v/v) | Relative luciferase expression (%) | Substance |
|---|---|---|---|---|
| H225 | A | 0 | 0.7 | — |
|  | A | 0 | 0.3 | 1% Ethanol |

TABLE-continued

| Cells | Complex | Glycerol % (v/v) | Relative luciferase expression (%) | Substance |
|---|---|---|---|---|
| | A | 0 | 4 | Chloroquine |
| | A | 0 | 0.8 | Bafilomycin A1 |
| | A | 10 | 100 | — |
| | A | 10 | 200 | 1% Ethanol |
| | A | 10 | 200 | 1.5% Ethanol |
| | A | 10 | 300 | Chloroquine |
| | A | 10 | 240 | Bafilomycin A1 |
| | B | 10 | 200 | 1.5% Ethanol |
| | B | 10 | 50 | — |
| | C | 10 | 95 | — |
| | D | 10 | 70 | — |
| NIH 3T3 | A | 0 | 0 | — |
| | A | 12.5 | 100 | — |
| | B | 0 | 0 | — |
| | B | 0 | 0 | Bafilomycin A1 |
| | B | 0 | 35 | Chloroquine |
| | B | 12.5 | 200 | — |
| | B | 12.5 | 350 | Bafilomycin A1 |
| | B | 12.5 | 80 | Chloroquine |
| | C | 0 | 0 | — |
| | C | 12.5 | 260 | — |
| | D | 0 | 0 | — |
| | D | 12.5 | 1000 | — |
| | B | 10 | 200 | — |
| | B | 10 | 1000 | Bafilomycin A1 |
| A549 | A | 0 | 0 | — |
| | A | 15 | 100 | — |
| | B | 0 | 0 | — |
| | B | 15 | 150 | — |
| | B | 15 | 170 | Chloroquine |
| | C | 15 | 130 | — |
| | D | 15 | 60 | — |
| primary fibroblasts | 4 × A | 0 | 0 | — |
| | 4 × A | 13 | 100 | — |
| | 4 × C | 0 | 0 | — |
| | 4 × C | 13 | 50 | — |

BIBLIOGRAPHY

Bowman, E. J., Siebers, A. and Altendorf, K., 1988, Proc.Natl.Acad.Sci. USA 85, 7972–7976.

Chen, C. A. and Okayama, H., 1988, BioTechniques 6, 632–638.

Cotten, M., Wagner, E., Zatloukal, K., Phillips, S., Curiel, D. and Birnstiel, M. L., 1992, Proc.Natl.Acad.Sci. USA 89, 6094–6098.

Curiel, D. T., Agarwal, S., Wagner, E. and Cotten, M., 1991, Proc.Natl.Acad.Sci. USA 88, 8850–8854.

Curiel, D. T., Agarwal, S., Romer, M. U., Wagner, E., Cotten, M., Birnstiel, M. L. and Boucher, R. C., 1992a, Am.J.Respir.Cell and Mol.Biol. 6, 247–252.

Curiel, D. T., Wagner, E., Cotten, M., Birnstiel, M. L., Agarwal, S., Li, Ch. -M., Loechel, S. and Hu, P. -H., 1992b, Human Gene Therapie 3, 147–154.

Gorman, C., 1985, DNA Cloning, A practical approach, Vol. 2, D. M. Glover (Ed.), 143–190.

Kasid, A., Morecki, S., Aebersold, P., Cornetta, K., Culver, K., Freeman, S., Director, E., Lotze, M. T., Blaese, R. M., Anderson, W. F. and Rosenberg, S. A., 1990, Proc.Natl.Acad.Sci. USA 87, 473–477.

Okada, C. Y. and Rechsteiner, M., 1982, Cell 29, 33–41.

Parker, B. A. and Stark, G. R., 1979, J. Virology 31, 360–369.

Seglen, P. O., 1983, Methods Enzymol. 96, 737–764.

Wagner, E., Zenke, M., Cotten, M., Beug, H. and Birnstiel, M. L., 1990, Proc.Natl.Acad.Sci. USA 87, 3410–3414.

Wagner, E., Cotten, M., Mechtler, K., Kirlappos, H. and Birnstiel, M. L., 1991, Bioconjugate Chemistry 2, 226–231.

Wagner, E., Zatloukal, K., Cotten, M., Kirlappos, H., Mechtler, K., Curiel, D. T. and Birnstiel, M. L., 1992, Proc.Natl.Acad.Sci. USA 89, 6099–6103.

Wilson, J. M., Danos, O., Grossman, M., Raulet, D. H. and Mulligan, R. C., 1990, Proc.Natl.Acad.Sci. USA 87, 439–443.

Wu, G. Y. and Wu, C. H., 1987, J. Biol. Chem. 262, 4429–4432.

Yoshimori, T., Yamamoto, A., Moriyama, Y., Futai, M. and Tashiro, Y., 1991, J. Biol. Chem. 266, 17707–17712.

Zatloukal, K., Wagner, E., Cotten, M., Phillips, S., Plank, C., Steinlein, P., Curiel, D. and Birnstiel, M. L., 1992, Ann.New York Acad.Sci. 660, 136–153.

We claim:

1. A method for introducing nucleic acids/polycation complexes into animal cells, said method comprising adding the complexes to the cells in the presence of a chemical selected from the group consisting of (a) ethyleneglycol, (b) glycerol, and (c) ethyleneglycol and glycerol.

2. The method according to claim 1, wherein the complexes are DNA/polylysine complexes.

3. The method according to claim 1, wherein the polycation is wholly or partially conjugated with an internalizing factor for the cells.

4. The method according to claim 3, wherein the internalizing factor is transferrin.

5. The method according to claim 3, wherein the internalizing factor/polycation conjugate is added in excess, so that the nucleic acids/polycation complexes are electro-positive.

6. The method according to claim 3, wherein the nonconjugated polycation and internalizing factor/polycation conjugate are added in excess, so that the nucleic acids/polycation complexes are electro-positive.

7. The method according to claim 3, wherein the nucleic acids are first mixed with a partial amount of the nonconjugated polycation, after which the majority of the internalizing factor/polycation conjugate is added.

8. The method according to claim 3, wherein the nucleic acids are first mixed with a partial amount of the nonconjugated polycation, after which the majority of nonconjugated polycation and internalizing factor/polycation conjugate is added.

9. The method according to claim 3, wherein the nucleic acids are first mixed with a partial amount of the internalizing factor/polycation conjugate, after which the majority of the nonconjugated polycation is added.

10. The method according to claim 3, wherein the nucleic acids are first mixed with a partial amount of the internalizing factor/polycation conjugate, after which the majority of the internalizing factor/polycation conjugate is added.

11. The method according to claim 3, wherein the nucleic acids are first mixed with a partial amount of the internalizing factor/polycation conjugate, after which the majority of the nonconjugated polycation and internalizing factor/polycation conjugate is added.

12. The method according to claim 3, wherein the nucleic acids are first mixed with a partial amount of the nonconjugated polycation and internalizing factor/polycation conjugate, after which the majority of the nonconjugated polycation is added.

13. The method according to claim 3, wherein the nucleic acids are first mixed with a partial amount of the nonconjugated polycation and internalizing factor/polycation conjugate, after which the majority of the internalizing factor/polycation conjugate is added.

14. The method according to claim 3, wherein the nucleic acids are first mixed with a partial amount of the nonconjugated polycation and internalizing factor/polycation conjugate, after which the majority of the nonconjugated polycation and internalizing factor/polycation conjugate is added.

15. The method according to claim 1, wherein the polycation is nonconjugated.

16. The method according to claim 15, wherein the nonconjugated polycation is added in excess, so that the nucleic acids/nolycation complexes are electro-positive.

17. The method according to claim 15, wherein the nucleic acids are first mixed with a partial amount of the nonconiugated polycation, after which the majority of the nonconjugated polycation is added.

18. The method according to claim 1, wherein the glycerol is in a concentration of about 8 to about 15%, based on the total volume of the transfection medium.

19. The method according to claim 1, wherein the cells are primary cells.

20. The method according to claim 19, wherein the primary cells are fibroblasts.

21. The method according to claim 1, further comprising adding the complexes to the cells in the presence of a chemical selected from the group consisting of (a) a substance which prevents the acidification of the endosomes, (b) a lower alcohol, and (c) a substance which prevents the acidification of the endosomes and a lower alcohol.

22. The method according to claim 1, wherein the complexes are added to the cells in the presence of chloroquine.

23. The method according to claim 1, wherein the complexes are added to the cells in the presence of bafilomycin.

24. The method according to claim 1, wherein the complexes are added to the cells in the presence of ethanol.

25. The method according to claim 1, wherein the glycerol is in a concentration of about 8 to about 13%, based on the total volume of the transfection medium.

26. A method for preparing cells which express a heterologous polypeptide from a stably transfected DNA molecule, the method comprising:
    (a) transfecting cells in the presence of a chemical selected from the group consisting of (i) glycerol ethyleneglycol, and (iii) glycerol and ethyleneglycol with a complex of a DNA molecule coding for the heterologous polypeptide and a polycation;
    (b) cultivating the cells, and
    (c) selecting stable cell clones.

27. The method according to claim 26, wherein the glycerol is in a concentration of about 8 to about 15%, based on the total volume of the transfection medium.

28. The method according to claim 28, wherein the cells are tumor cells.

29. The method according to claim 28, wherein the heterologous polypeptide is an immuno-stimulant polypeptide.

30. The method according to claim 28, wherein the heterologous polypeptide is a cytokine.

31. The method according to claim 26, wherein the glycerol is in a concentration of about 8 to about 13%, based on the total volume of the transfection medium.

32. The method according to claim 26, further comprising (d) establishing cell lines from the selected clones.

33. The method according to claim 32, wherein the glycerol is in a concentration of about 8 to about 15%, based on the total volume of the transfection medium.

34. The method according to claim 32, where the glycerol is in a concentration of about 8 to about 13%, based on the total volume of the transfection medium.

35. The method according to claim 26, wherein the polycation is wholly or partially conjugated with an internalizing factor.

36. The method according to claim 35, wherein the glycerol is in a concentration of about 8 to about 15%, based on the total volume of the transfection medium.

37. The method according to claim 35, wherein the glycerol is in a concentration of about 8 to about 13%, based on the total volume of the transfection medium.

38. The method according to claim 35, further comprising (d) establishing cell lines from the selected clones.

39. The method according to claim 38, wherein the glycerol is in a concentration of about 8 to about 15%, based on the total volume of the transfection medium.

40. The method according to claim 38, wherein the glycerol is in a concentration of about 8 to about 13%, based on the total volume of the transfection medium.

41. The method according to claim 26, further comprising adding the complexes to the cells in the presence of a chemical selected from the group consisting of (a) a substance which prevents the acidification of the endosomes, (b) a lower alcohol, and (c) a substance which prevents the acidification of the endosomes and a lower alcohol.

42. A medium for transfection of animal cells, the medium comprising:
    (a) nutrients and conventional additives, as the active components;
    (b) complexes of nucleic acid and a polycation which is selected from the group consisting of (i) nonconjugated polycation (ii) polycation fully conjugated with an internalizing factor of the cells, and (iii) polycation partially conjugated with an internalizing factor of the cells, and
    (c) a chemical selected from the group consisting of (i') ethyleneglycol (ii') glycerol, and (iii') ethyleneglycol and glycerol.

43. The medium according to claim 42, wherein the glycerol is in a concentration of about 8 to about 15%, based on the total volume.

44. The medium according to claim 42, further comprising (d) a chemical selected from the group consisting of (i") a substance which prevents the acidification of the endosomes, (ii") a lower alcohol, and (iii") a substance which prevents the acidification of the endosomes and a lower alcohol.

45. The medium according to claim 42, further comprising (d) chloroquine.

46. The medium according to claim 42, further comprising (d) bafilomycin.

47. The medium according to claim 42, further comprising (d) ethanol.

48. The medium according to claim 42, wherein the glycerol is in a concentration of about 8 to about 13% of glycerol, based on the total volume.

49. The method according to claim 48, wherein the cells are melanoma cells and the cytokine is interleukin-2.

* * * * *

UNITED STATES PATENT AND TRADEMARK OFFICE
CERTIFICATE OF CORRECTION

PATENT NO. : 5,965,404  
DATED : October 12, 1999  
INVENTOR(S) : Buschle et al.

Page 1 of 2

It is certified that error appears in the above-indentified patent and that said Letters Patent is hereby corrected as shown below:

On the title page:

item [73] ("Assignee"), please delete "FmbH" and insert therein --GmbH--.

Column 13, at claim 16, line 9, please delete "nolycation" and insert therein --polycation--.

Column 13, at claim 17, line 12, please delete "nonconiugated" and insert therein --nonconjugated--.

Column 13, at claim 26, line 40, after "glycerol", please insert --, (ii)--, and line 44, please delete "," and insert therein --;--.

Column 13, at claim 28, line 49, please delete "claim 28" and insert therein --claim 26--.

UNITED STATES PATENT AND TRADEMARK OFFICE
CERTIFICATE OF CORRECTION

PATENT NO. : 5,965,404
DATED : October 12, 1999
INVENTOR(S) : Buschle et al

It is certified that error appears in the above-indentified patent and that said Letters Patent is hereby corrected as shown below:

Column 14, at claim 34, line 1, please delete "where" and insert therein --wherein--.

Column 14, at claim 42, line 30, please delete ", as the active components" and line 32, after "(b)", please insert --as the active components,--.

Column 14, at claim 42, line 35, please delete "polycation (ii)" and insert therein --polycation, (ii)--, at line 38, please delete "," and insert therein --;--, and at line 40, please delete "ethyleneglycol (ii')" and insert therein --ethyleneglycol, (ii')--.

Column 14, at claim 49, line 60, please delete "48" and insert therein --30--.

Signed and Sealed this

Twenty-fourth Day of April, 2001

Attest:

NICHOLAS P. GODICI

Attesting Officer      Acting Director of the United States Patent and Trademark Office